United States Patent

Veber et al.

[11] 4,254,107
[45] Mar. 3, 1981

[54] LONG-LASTING AGONISTS OF ENKEPHALIN

[75] Inventors: Daniel F. Veber, Ambler; Roger M. Freidinger, Hatfield, both of Pa.

[73] Assignee: Merck & Co., Inc., Rahway, N.J.

[21] Appl. No.: 97,758

[22] Filed: Nov. 27, 1979

[51] Int. Cl.$^3$ .................... A61K 37/00; C07C 103/52; A01N 43/84; C07D 209/18; C07D 279/04; C07D 401/00; C07D 211/22

[52] U.S. Cl. .................... 424/177; 424/246; 260/112.5 R; 424/263; 424/274; 424/244; 260/326.13 R; 548/336

[58] Field of Search .................... 260/112.5 R, 326.42, 260/329.3 R, 326.13 R; 424/177, 246, 263, 274, 244; 544/54; 546/201, 221, 210; 548/336

[56] References Cited

FOREIGN PATENT DOCUMENTS 2008121  5/1979  United Kingdom .................... 424/177

OTHER PUBLICATIONS

Hughes, J. et al., Nature 258, 577–579 (1975).
Restak, Sat. Rev., 3-5-77, pp. 7–11.
Snyder, C&EN, Nov. 28, 1977, 26–35.
Pert et al., Nature 269, 73–75, 1977.
Klee, "Endogenous Opiate Peptides," *Peptides in Neurobiology*, Plenun Press, N.Y., pp. 375–396 (1977).
C&EN, Aug. 16, 1976, pp. 18–19.
Heterocycles 9, No. 7, pp. 831–849.

*Primary Examiner*—Delbert R. Phillips
*Attorney, Agent, or Firm*—Raymond M. Speer; Mario A. Monaco

[57] ABSTRACT

Novel peptides of the formula:

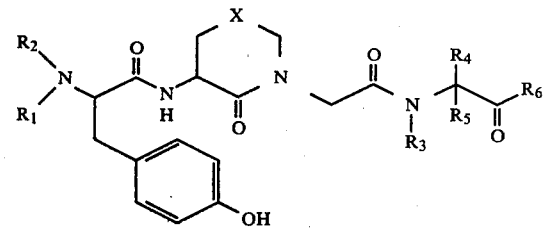

wherein X is S or $(CH_2)_n$ and n is 0, 1 or 2, and $R_1$ through $R_6$ are various amino acid and other substituents; having long-lasting enkephalin agonist activity; useful in treating pain and in treating schizophrenia.

37 Claims, No Drawings

LONG-LASTING AGONISTS OF ENKEPHALIN

BACKGROUND OF THE INVENTION

1. Field of the Invention

The present invention is concerned with novel peptide compounds having long-lasting enkephalin agonist activity, with pharmaceutical compositions containing said novel peptide compounds as active ingredients, with use of said novel peptide compounds in methods of treating pain and schizophrenia, and with a novel method of preparing the novel peptide compounds of the present invention wherein X is sulfur.

2. Brief Description of the Prior Art

Enkephalin is an endogenous, morphine-like pentapeptide discovered by Hughes and Kosterlitz in 1975 (Hughes, J. et al., *Nature*, 258, 577–579, 1975) which may have either of the following two structures:
Methionine enkephalin: Tyr-Gly-Gly-Phe-Met
Leucine Enkephalin: Tyr-Gly-Gly-Phe-Leu Since the discovery of enkephalin, a great deal of activity has been devoted to investigating the mode of action of enkephalin, as well as the properties of various synthetic analogs of enkephalin. See, for example, Restak, Sat. Rev., 3-5-77, pp. 7–11; Snyder, *C&EN*, Nov. 28, 1977, pp. 26–35; Pert et al., *Nature*, 269, 73–75, 1977; Klee, "Endogenous Opiate Peptides", *Peptides in Neurobiology*, Plenum Press, N.Y., pp. 375–396, 1977; *C&EN*, Aug. 16, 1976, pp. 18–19; and British Pat. No. 2,008,121.

With regard to the novel method of preparing the novel peptide compounds of the present invention wherein X is sulfur, while Kametani et al., in *Heterocycles*, Vol. 9, No. 7, pp. 831–840 (1978), disclose an acid-catalyzed cyclization reaction of secondary amides possessing a mercapto group at the with aldehydes to give tetrahydro-1,3-thiazin-4-ones, there is no teaching or suggestion therein that the method disclosed therein would be useful in preparing compounds of the type represented by the novel peptide compounds of the present invention wherein X is sulfur.

SUMMARY OF THE INVENTION

The present invention concerns novel peptides of the formula:

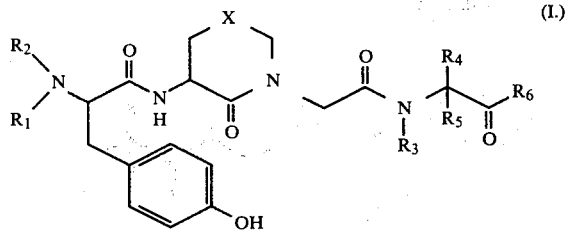

(I.)

where, unless otherwise indicated, an amino acid has the "S—" stereoconfiguration:

$X$ is S or $(CH_2)_n$, where n is 0, 1 or 2;

$R_1$ is hydrogen; $C_{1-6}$ alkyl; H-Arg (Arginine); or H-Lys-Arg (Lysine-Arginine);

$R_2$ is hydrogen; $C_{1-6}$ alkyl; or, when $R_1$ is hydrogen, may be allyl or cyclopropylmethyl;

$R_3$ is hydrogen or methyl;

$R_4$ is benzyl; benzyl substituted with halo, nitro, hydroxy, amino, $C_{1-4}$ alkyl, or cyano; indolylmethyl; imidazolylmethyl; or isopropylmethyl;

$R_5$ is hydrogen or methyl;

$R_4$ and $R_5$ taken together are phenylmethylene; and $R_6$ is (a) OM, where M is hydrogen, $C_{1-6}$ alkyl, or a cation; (b) $NR_7R_8$ where $R_7$ and $R_8$ are independently selected from the group consisting of hydrogen; $C_{1-6}$ alkyl, and, when either of $R_7$ or $R_8$ is hydrogen, $-CH_2CH_2N(CH_3)_2$ and

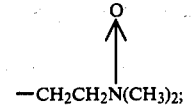

(c) Met-OH (Methionine as acid); (d) Met-NH$_2$ (Methionine as amido); (e) Met-ol (Methionine as alcohol); (f) D-Met-NH$_2$; (g) N-methyl-Met-NH$_2$; (h) Met(O)-NH$_2$ (Methionine sulfoxide as amide); (i) Met(O)-ol; (j) Leu-NH$_2$ (Leucine as amide); (k) N-methyl-Leu-NH$_2$; (l) D-Leu-NH$_2$; or (m) Pro-NH$_2$ (Proline as amide).

Preferred novel peptides of the present invention are those of Formula I. wherein:

X is sulfur or $(CH_2)_n$ where n is 1;

$R_1$ and $R_2$ are hydrogen;

$R_3$ and $R_5$ are hydrogen or methyl;

$R_4$ is benzyl;

$R_4$ and $R_5$ taken together are phenylmethylene; and $R_6$ is $NR_7R_8$ where one of $R_7$ or $R_8$ is hydrogen and the other is $-CH_2CH_2\ N(CH_3)_2$ or

Met-OH; Met-NH$_2$; Met-ol; D-Met-NH$_2$; N-methyl-Met-NH$_2$; Met(O)-NH$_2$: Met(O)-ol; Leu-NH$_2$; N-methyl-Leu-NH$_2$; D-Leu-NH$_2$; or Pro-NH$_2$.

In the novel peptides of the present invention it is preferred that the lactam bridge at the 2-position have a "R—" stereoconfiguration, although the "S—" configuration may also be employed.

Thus, the following are preferred specific novel peptides of the present invention:

H-Tyr-2-[R-(3-amino-2-oxo-1-piperidine)acetic acid]-[N-methyl-Phe]-Met-NH$_2$

H-Tyr-2-[R-(3-amino-2-oxo-1-piperidine)acetic acid]-[N-methyl-Phe]-Met-ol

H-Tyr-2-[R-(3-amino-2-oxo-1-piperidine)acetic acid]-[N-methyl-Phe]-Met(O)-NH$_2$ H-Tyr-2-[R-(3-amino-2-oxo-1-piperidine)acetic acid]-[N-methyl-Phe]-Met(O)-ol H-Tyr-2-[R-(3-amino-2-oxo-1-piperidine)acetic acid]-[N-methyl-Phe]-N-methyl-Met-NH$_2$ H-Tyr-2-[R-(3-amino-2-oxo-1-piperidine)acetic acid]-[N-methyl-Phe]-D-Met-NH$_2$ H-Tyr-2-[R-(3-amino-2-oxo-1- piperidine)acetic acid]-[N-methyl-Phe]-Leu-NH$_2$ H-Tyr-2-[R-(3-amino-2-oxo-1-piperidine)acetic acid]-[N-methyl-Phe]-N-methyl-Leu-NH$_2$ H-Tyr-2-[R-(3-amino-2-oxo-1-piperidine)acetic acid]-[N-methyl-Phe]-D-Leu-NH$_2$ H-Tyr-2[R-(3-amino-2-oxo-1-piperidine)acetic acid]-[N-methyl-Phe]-Pro-NH$_2$ H-Tyr-2-[R-(3-amino-2-oxo-1-piperidine)acetic acid]-[N-methyl-Phe]

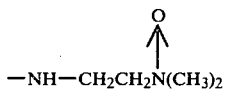

H-Tyr-2-[R-(3-amino-2-oxo-1-piperidine)acetic acid]-[N-methyl-Phe]-NH-CH2CH2N(CH3)2
H-Tyr-2-[R-(3-amino-2-oxo-1-piperidine)acetic acid]-[α-methyl-Phe]-Met-NH2
H-Tyr-2-[R-(3-amino-2-oxo-1-piperidine)acetic acid]-[α-methyl-Phe]-Met-ol
H-Tyr-2-[R-(3-amino-2-oxo-1-piperidine)acetic acid]-[α-methyl-Phe]-Met(O)-NH2
H-Tyr-2-[R-(3-amino-2-oxo-1-piperidine)acetic acid]-[α-methyl-Phe]-Met(O)-ol
H-Tyr-2-[R-(3-amino-2-oxo-1-piperidine)acetic acid]-[αmethyl-Phe]-N-methyl-Met-NH2
H-Tyr-2-[R-(3-amino-2-oxo-1-piperidine)acetic acid]-[α-methyl-Phe]-D-Met-NH2
H-Tyr-2-[R-(3-amino-2-oxo-1-piperidine)acetic acid]-[α-methyl-Phe]-Leu-NH2
H-Tyr-2-[R-(3-amino-2-oxo-1-piperidine)acetic acid]-[α-methyl-Phe]-N-methyl-Leu-NH2
H-Tyr-2-[R-(3-amino-2-oxo-1-piperidine)acetic acid]-[α-methyl-Phe]-D-Leu-NH2
H-Tyr-2-[R-(3-amino-2-oxo-1-piperidine)acetic acid]-[α-methyl-Phe]-Pro-NH2
H-Tyr-2-[R-(3-amino-2-oxo-1-piperidine)acetic acid-[α-methyl-Phe]

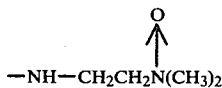

H-Tyr-2-[R-(3-amino-2-oxo-1-piperidine)acetic acid]-[α-methyl-Phe]-NH-CH2CH2N(CH3)2
H-Tyr-2-[R-(3-amino-2-oxo-1-piperidine)acetic acid]-[2,3-dehydro Phe]-Met-NH2
H-Tyr-2-[R-(3-amino-2-oxo-1-piperidine)acetic acid]-[2,3-dehydro Phe]-Met(O)-ol
H-Tyr-2-[R-(3-amino-2-oxo-1-piperidine)acetic acid]-[2,3-dehydro Phe]-N-methyl-Leu-NH2
H-Tyr-2-[R-(3-amino-2-oxo-1-piperidine)acetic acid]-[2,3-dehydro Phe]

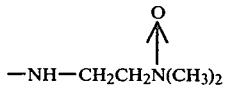

H-Tyr-2-[R-(3-amino-2-oxo-1-piperidine)acetic acid]-[2,3-dehydro Phe]-NH-CH2CH2N(CH3)2
H-Tyr-2-[R-(5-amino-4-oxo-1,3-thiazine)acetic acid]-[N-methyl-Phe]-Met-NH2
H-Tyr-2-[R-(5-amino-4-oxo-1,3-thiazine)acetic acid]-[N-methyl-Phe]-Met(O)-ol
H-Tyr-2-[R-(5-amino-4-oxo-1,3-thiazine)acetic acid]-[N-methyl-Phe]-N-methyl-Leu-NH2
H-Tyr-2-[R-(5-amino-4-oxo-1,3-thiazine)acetic acid]-[N-methyl-Phe]

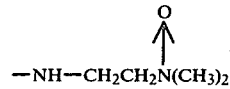

H-Tyr-2-[R-(5-amino-4-oxo-1,3-thiazine)acetic acid]-[N-methyl-Phe]-NH-CH2CH2N(CH3)2

The novel peptides of the present invention have as an essential feature a lactam conformation constraining bridge which essentially replaces the Gly-Gly 2- and 3-position dipeptide in both Methionine enkephalin and Leucine enkephalin.

In accordance with the present invention there is also provided a method of treating pain comprising administering to a patient in need of such treatment, a therapeutically effective amount of a peptide of the formula:

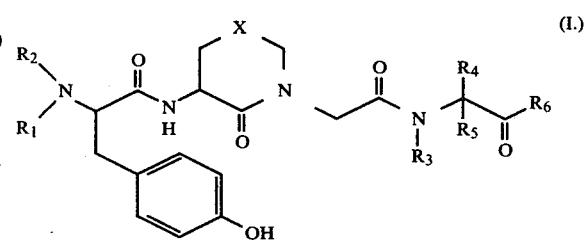

(I.)

wherein, unless otherwise indicated, an amino acid has the "S—" stereoconfiguration:

X is S or $(CH_2)_n$, where n is 0, 1, or 2;
$R_1$ is hydrogen; $C_{1-6}$ alkyl; H-Arg; or H-Lys-Arg;
$R_2$ is hydrogen; $C_{1-6}$ alkyl; or, where $R_1$ is hydrogen, may be allyl or cyclopropylmethyl;
$R_3$ through $R_6$ are as described above.

Dosage levels of the order of 20 μg. to 20 mg. per day are useful in the treatment of pain. Thus, pain is effectively treated by the administration of from about 0.3 μg. to 0.3 milligrams of the peptide per kilogram of body weight per day. Advantageously, from about 1 μg. to about 100 μg. per kilogram of body weight per daily dosage produces highly effective results.

In accordance with the present invention there is further provided a method of treating schizophrenia comprising administering to a patient in need of such treatment, a therapeutically effective amount of a peptide of the formula:

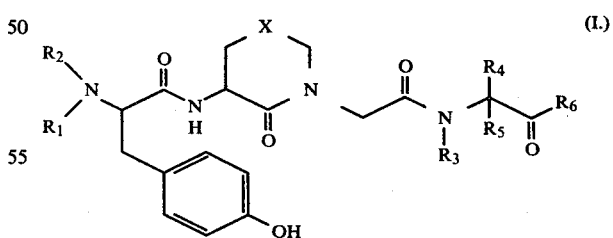

(I.)

wherein, unless otherwise indicated, an amino acid has the "S—" stereoconfiguration:

X is S or $(CH_2)_n$, where n is 0, 1 or 2;
$R_1$ is hydrogen; $C_{1-6}$ alkyl; H-Arg; or H-Lys-Arg;
$R_2$ is hydrogen; $C_{1-6}$ alkyl; or, when $R_1$ is hydrogen, may be allyl or cyclopropylmethyl; and
$R_3$ through $R_6$ are as described above.

Dosage levels of the order of 20 μg. to 20 mg. per day are useful in the treatment of schizophrenia. Thus, schizophrenia is effectively treated by the administration of from about 0.3 µg. to 0.3 milligrams of the peptide per kilogram of body weight per day. Advantageously, from about 1 µg. to about 100 µg. per kilogram of body weight per daily dosage produces highly effective results.

For each of the methods of treatment of the present invention, the amount of active ingredient that may be combined with the carrier materials to produce a single dosage form will vary depending upon the host treated and the particular mode of administration. For example, a formulation intended for the oral administration of humans may contain from 5 µg. to 20 mg. of active agent compounded with an appropriate and convenient amount of carrier material which may vary from about 5 to about 95 percent of the total composition. Dosage unit forms will generally contain between from about 20 µg. to about 10 mg. of active ingredient.

It will be understood, however, that the specific dose level for any particular patient will depend upon a variety of factors including the activity of the specific compound employed, the age, body weight, general health, sex, diet, time of administration, route of administration, rate of excretion, and drug combination.

In accordance with the present invention there is further provided pharmaceutical compositions for use in treating pain and schizophrenia. The novel peptides of the present invention possess enkephalin agonist activity and are long-acting.

For these purposes the novel peptides of the present invention may be administered orally, topically, parenterally, by inhalation spray, intravaginally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the peptides of the present invention are effective in the treatment of humans.

The pharmaceutic compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example, starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethyl-cellulose, methyl-cellulose, hydroxypropylmethylcellulose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acid anhydrides and hexitol, for example polyoxyethylene sorbitan monooleate, the said aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspension may contain a thickening agent, for example beeswax, hard paraffin or cetyl alcohol. Sweetening agents, such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example liquid paraffin or mixtures of these. Suitable emulsifying agents may be naturally-occurring gums, for example gum acacia or gum tragacant, naturally-occurring phosphatides, for example soya bean lecithin, and esters of partial esters derived from fatty acid anhydrides and hexitol, for example sorbitan mono-oleate, and condensation products of the said partial esters with ethylene oxide, for example polyoxyethylene sorbitan mono-oleate. The emulsions may also contain sweetening and flavouring agents.

Syrups and elixirs may be formulated with sweetening agents, for example glycerol, sorbitol or sucrose. Such formulations may also contain a demulcent, a preservative and flavouring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The peptides of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are coca butter and polyethylene glycols.

The novel peptides of the present invention, with respect to the various amino acid substituents of the peptide, are prepared in accordance with well-known methods in the art for the synthesis of peptides. However, the different forms of the unique lactam bridge in the novel peptides of the present invention are prepared by processes not heretofore known in the art or by a novel method of preparation of the present invention.

In the novel peptides of Formula I. where X is $CH_2$ and n is 0, the resulting 5-membered lactam bridge may be prepared in accordance with the procedures described in copending application Ser. No. 080,844, filed Oct. 1, 1979, and incorporated herein by reference, employing Met-Gly rather than Met-Leu.

In the novel peptides of Formula I. where X is $CH_2$ and n is 1, the resulting 6-membered lactam bridge may be prepared in accordance with the procedures described in copending application Ser. No. 008,904, filed Feb. 2, 1979, and incorporated herein by reference. For the corresponding 7-membered lactam, where X is $CH_2$ and n is 2, the same method may be utilized, except that the starting material is a protected Lysine (Lys) derivative, rather than a protected Ornithine (Orn) derivative. Preparation of the 7-membered lactam may be illustrated by way of the following reaction diagram:

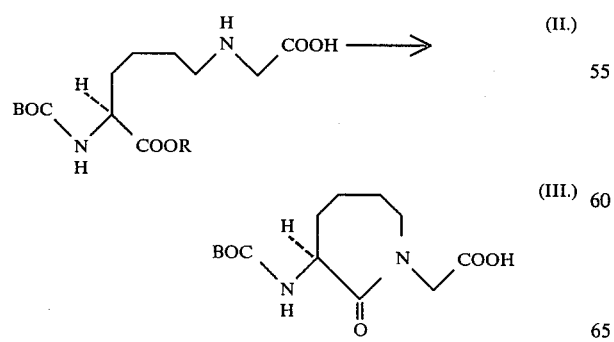

where BOC is tert-butyloxycarbonyl, and R is $C_{1-4}$alkyl.

In the novel peptides of Formula I. where X is S, the resulting 6-membered sulfur lactam, or thiazine, bridge may be prepared in accordance with the procedures of the novel method of preparation of the present invention. This method may be illustrated by the following reaction diagram:

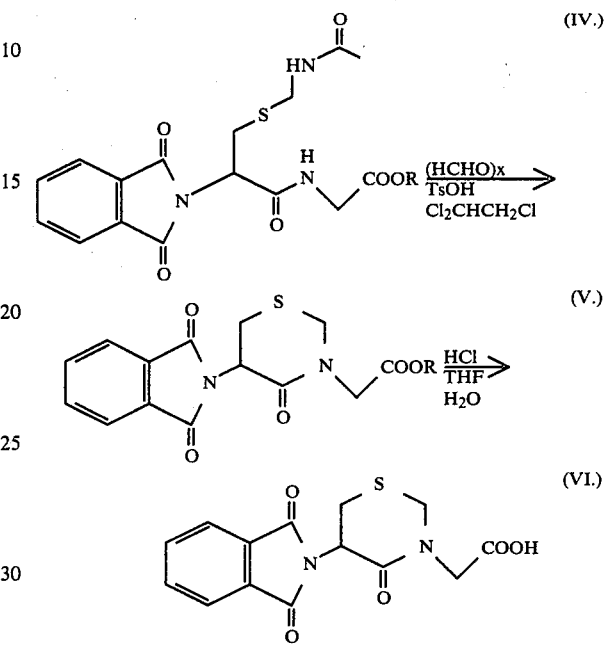

where R is $C_{1-4}$alkyl.

In the first step of the novel preparation method of the present invention, there may be used as the starting material, for example, the methyl ester of the Cysteine-Glycine dipeptide: Cys-Gly-OMe. The Cys portion of the dipeptide is blocked at one end by a phthalic radical, thus forming a phthalimido group, and at the other end with an acetamidomethyl group.

The starting material may be prepared by conventional means from phthalimido and acetamidomethyl blocked Cys, and from Gly methyl ester, using, for example, diphenylphosphorylazide in dimethylformamide as the coupling agent, at 0° C.

The starting material is treated with paraformaldehyde, using a strong acid catalyst, preferably toluenesulfonic acid, under anhydrous conditions. The solvent employed is one with a boiling point of from 80°–150° C., for example, an aromatic hydrocarbon or a halogenated hydrocarbon, preferably 1,1,2-trichloroethane. It is preferred that the reaction be carried out under a nitrogen atmosphere, and at the reflux temperature of the solvent.

The first step reaction effects removal of the acetamidomethyl group, followed by ring closure of the Cys-Gly-OMe dipeptide.

The second step involves hydrolysis the dipeptide ester prepared in the first step. This hydrolysis may be carried out by conventional means, for example, using concentrated hydrochloric acid in water and tetrahydrofuran.

The resulting compound of Formula VI. is a novel compound and also forms a part of the present invention.

The novel preparation method of the present invention may thus be described as a method of preparing a compound of the formula:

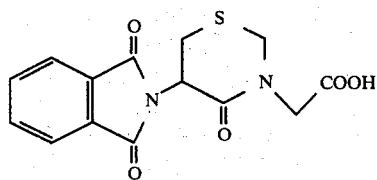

comprising the steps of:
(a) treating a phthalyl and acetamidomethyl protected Cys-Gly-OMe dipeptide of the formula:

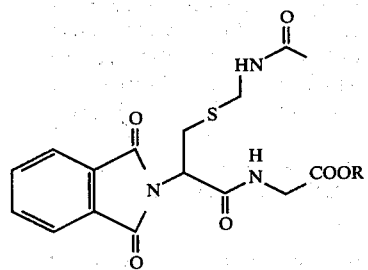

where R is $C_{1-4}$ alkyl, with paraformaldehyde, in the presence of a strong acid catalyst, under anhydrous conditions, and in an aromatic hydrocarbon or halogenated hydrocarbon solvent having a boiling point of from 80°–150° C.; to form a thiazine ester; and
(b) hydrolyzing the thiazine ester prepared in step (a) to form the corresponding acid of Formula (VI.).

EXAMPLE 1

3-Carbomethoxymethyl-4-oxo-5-phthalimido-1,3-thiazine

A 210 mg. (0.53 mmole) sample of phthalimido-Cys (acetamidomethyl blocked)-Gly-OMe was dissolved in 5 ml. of methanol under a nitrogen atmosphere with stirring. To this solution was added 5 ml. of 0.1 N acetic acid followed by 172 mg. (0.54 mmole) of mercuric acetate. A complete solution was obtained. After 1 hr., a small amount of precipitate was present. Addition of 10 ml. of 0.1 N acetic acid gave more precipitate. This white solid was filtered and then redissolved in 5 ml. of methanol and 5 ml. of 0.1 N acetic acid, and several drops of glacial acetic acid were added. Hydrogen sulfide gas was bubbled through this solution as well as the filtrate, and mercuric sulfide precipitated from both solutions. Since good separation of product from N-(hydroxymethyl) acetamide was not obtained, the two solutions were filtered and the filtrates were combined and concentrated in vacuo. The semisolid residue was triturated with water. The insoluble gum was substantially free of byproducts, but the three water washes contained some product as well as the byproducts. The water solution was concentrated in vacuo and the resulting residue was triturated with water. A total of about 100 mg. of free thiol (based on the Ellman test) relatively free of N-(hydroxymethyl) acetamide was obtained.

The thiol was dissolved in 5 ml. of methanol and diluted with 5 ml. of xylene. To this solution was added p-toluenesulfonic acid monohydrate (50 mg.) and paraformaldehyde (150 mg.). Heat was applied to the solution to distill off the methanol and then refluxed for 2 hrs. At this point a brown gum had separated and the Ellman test was negative. The xylene was removed in vacuo and the brown residue was dissolved in methanol. Thin layer chromatography on a 1000µ silica gel Q-1F plate developing with 98:2 chloroform: methanol and eluting the main band with 4:1 chloroform: methanol gave 60 mg. of a light yellow gum. This sample crystallized from ethyl acetate: hexane overnight at 5° C. in the form of two yellow clumps. The flask was placed at −20° C. for several hours and small white crystals separated. The mother liquor was decanted and the crystals were washed with 4:1 hexane: ethyl acetate. After drying in vacuo, the two types of crystals were separated by hand. The clump crystals (11.8 mg.) had a m.p. of 177° C., and the white crystals (18.9 mg.) had a m.p. of 140°–165° C. The nmr spectrum of the white crystal product showed it to be a mixture of the desired product and at least one other substance.

EXAMPLE 2

H-Tyr-2-[R-(4-oxo-5-amino-1,3-thiazine)acetic acid]-Phe-Met-NH$_2$

A. 3-Carbomethoxymethyl-4-oxo-5-phthalimido-1,3-thiazine

A 101 mg. (0.26 mmole) sample of phthalimido-D-Cys(acetamidomethyl blocked)-Gly-OMe was added to 5 ml. of 1,1,2-trichloroethane under nitrogen, and p-toluenesulfonic acid (49 mg.) and paraformaldehyde (149 mg.) were added. The reaction mixture was refluxed for 5 hrs. and became homogeneous after heating. After cooling, the reaction mixture was concentrated in vacuo, and the resulting residue was subjected to thin layer chromatography as described above in Example 1, giving 73 mg. of desired product (84% yield). The product was crystallized from ethyl acetate and had a m.p. of 181°–183° C.

B. 3-Carboxymethyl-4-oxo-5-phthalimido-1,3-thiazine

A 24 mg. (0.07 mmole) sample of the methyl ester product obtained in Step A. above, in a solution of 1.5 ml. of tetrahydrofuran, 0.5 ml. of water, and 0.25 ml. of concentrated hydrochloric acid, was refluxed under nitrogen for 3.5 hrs. The solution was cooled and diluted with 5 ml. of water and then extracted four times with a total of 15 ml. of dichloromethane. The organic phase was dried over sodium sulfate and concentrated in vacuo. The resulting residue was triturated with dichloromethane and crystals formed, which were washed with dichloromethane and dried to give 10.1 mg. of product having a m.p. of 227°–228° C. The mother liquor on concentration in vacuo also crystallized to give 13.3 mg. of product.

C. [2-(4-oxo-5-phthalimido-1,3-thiazine)acetic acid]-Phe Met-NH$_2$

A 2 g. (0.00625 mole) sample of the acid product obtained in Step B. above was dissolved with stirring in 40 ml. of degassed dimethylformamide and cooled under nitrogen to 0° C. Phe-Met-NH$_2$ as hydrochloride was dissolved separately in 20 ml. of dimethylformamide and cooled to 0° C. To the acid solution was added 1.48 ml. (0.00688 mole) of diphenylphosphorylazide (DPPA) in one portion followed by 0.96 ml. (0.00688 mole) of triethylamine. The Phe-Met-NH$_2$ solution was then added and the reaction mixture was stirred at 0° C. for 3 hrs. and then at room temperature for 16 hrs. The dimethylformamide was concentrated down and the residue was taken up in dichloromethane. The first wash with aqueous 1 N hydrochloric acid caused immediate crystallization through both layers. The crystals in both layers were filtered and washed twice with 1 N hydrochloric acid, three times with 1 N sodium hydrogencarbonate, and once with hexane, then dried in vacuo. The filtrate was washed three times with 1 N hydrochloric acid and three times with 1 N sodium hydrogencarbonate, then dried over sodium sulfate and concentrated to a crystalline mass. The first crop (filtered) was 2.57 g. and had a m.p. of 192°–195° C. The second crop (filtrate) was 696 mg. and had a m.p. of 189°–193° C. The combined yield was 88%.

D. [2-(4-oxo-5-amino-1,3-thiazine)acetic acid]-Phe-Met-NH$_2$ acetate

To a 3.0 g. (5 mmole) sample of the product obtained in Step C. above was added 100 ml. of ethanol. This was followed by 0.48 ml. (2 eq.) of methylhydrazine along with 12 drops of acetic acid. The reaction mixture was refluxed for 16 hrs. under nitrogen. The reaction mixture was then concentrated from methanol until the methylhydrazine was gone by Tollens test. The residue was triturated with water in order to precipitate methyl phthalyl hydrazide. The precipitate was filtered and the procedure was repeated. The product was precipitated from ethyl acetate/hexane and 50 ml. of acetone was added, followed by heating of the solution on a rotoevaporator at 50° C. for 30 min. to evaporation of the solvent. The procedure was repeated using methanol, and the product was again precipitated from ethyl acetate/hexane and carried through the next step without further treatment.

E. BOC-Tyr-2-[R-(4-oxo-5-amino-1,3-thiazine)acetic acid]-Phe-Met-NH$_2$

The acetic acid addition salt product obtained in Step D. above and 1.98 g. (5.25 mmole) of hydroxysuccinimide ester of t-butyloxycarbonyl (BOC) protected Tyr were dissolved in 25 ml. of degassed dimethylformamide under nitrogen at room temperature. The pH of the reaction mixture was brought to 8.5 by addition of triethylamine with stirring, and stirring was continued overnight. The reaction mixture was then added in one portion to 100 ml. of water, which was then extracted three times with dichloromethane. The combined extracts were dried over sodium sulfate and then concentrated. Product separation was performed on a Water's HPLC using 21 l. of 28% cyanomethane in ammonium acetate buffer. Fraction 12 was freeze dried directly from the system, and then twice from water to give 106 mg. of the R-diastero isomer product.

F. Deblocking of BOC-Tyr-2-[R-(4-oxo-5-amino-1,3-thiazine) acetic acid]-Phe-Met-NH$_2$ The 106 mg. of product obtained in Step E. above was added to 10 ml. of 25% trifluoroacetic acid (TFA) containing 1% ethanedithiol (EDT) and stirred at room temperature under a nitrogen atmosphere for 15 min. The reaction mixture was then washed three times each, alternatingly, with dichloromethane and methanol. The product was precipitated from methanol/ethyl acetate/hexane to yield 62 mg.

EXAMPLE 3

H-Tyr-2-[R-(3-amino-2-oxo-1-azepine)acetic acid]-Phe-Met-NH$_2$

A. Reductive alkylation of α-BOC-2-Cl-CBZ-R-Lys-OMe

An 18 g. (42 mmole) sample of the t-butyloxycarbonyl (BOC) and benzyloxycarbonyl (CBZ) protected starting material: α-BOC-2-Cl-CBZ-R-Lys-OMe and 4.76 g. of glyoxylic acid hydrate were dissolved in 112 ml. of methanol in a Parr bottle, and 1.4 g. of 10% palladium carbon catalyst was added. The reaction mixture was hydrogenated on a Parr shaker at about 40 p.s.i. After 13.5 hrs. removal of the Cl-CBZ group was complete, but the reductive alkylation was only about 50% complete. The reaction was very slow after this point and had gone little further after 3 days. Additional glyoxylic acid (1.5 g.) and acetic acid (3 ml.) were added, but with little effect. The reaction was terminated after 4 days, the catalyst was filtered and washed with methanol, and the filtrate was concentrated in vacuo to give a viscous oil crude product which was carried through the next step without further purification.

B. 2-(R-3-BOC-amino-2-oxo-1-azepine)acetic acid

The crude product obtained in Step A. above was dissolved in 2200 ml. of acetonitrile, and 10 ml. of triethylamine was added. The solution was refluxed for 6 days followed by concentration in vacuo. The residue was dissolved in 100 ml. of dichloromethane, and then extracted three times with 40 ml. of concentrated aqueous citric acid, and then twice with 40 ml. of 1 N sodium hydrogencarbonate. The sodium hydrogencarbonate extracts were combined and acidified with concentrated aqueous citric acid, and then extracted six times with 50 ml. of dichloromethane. The dichloromethane extracts were combined, dried over sodium sulfate, and the dichloromethane was removed in vacuo to obtain the product as a white foam with 19% yield (2.27 g.)

C. 2-[R-(3-BOC-amino-2-oxo-1-azepine)acetic acid]-Phe-Met-NH$_2$

The following resin peptide was first prepared: 2-[R-(3-BOC-amino-2-oxo-1-azepine)acetic acid]-Phe-Met-OR (where R indicates a Merrifield Resin moiety), starting with BOC-Phe-Met-OR and the product obtained in Step B. above. The following procedures were followed.

Chloromethyl resin (2% cross-linked Merrifield resin), 862.0 g. (2.37 moles), having 2.75 meq. chlorine/g., and 590.6 g. (2.37 moles, 1 equivalent) of BOC-Met were added to 4320 ml. of peroxide-free tetrahydrofuran. The mixture was stirred in an oil bath at 80° C. bath temperature for 45 minutes. Triethylamine, 310.0 ml., was added and the reaction mixture stirred at 80° C. bath temperature for 70 hours, cooled to 25° C. and transferred to a stirred solid phase reaction column with 2000 ml. of tetrahydrofuran. After removal of the solvent, the resin was washed using the stirred column with:

3×2000 ml. of tetrahydrofuran
4×5170 ml. of ethanol
1×5170 ml. of acetic acid
3×5170 ml. of water
3×5170 ml. of methanol 3×5170 ml. of chloroform The BOC-Met-O-CH$_2$-φ-resin was dried in vacuo at 25° C. for 16 hours, giving 1170 g. of BOC-Met-O-CH$_2$-φ-resin containing 0.9 mmole of methionine/g. of resin.

BOC-Met-O-CH$_2$-φ-resin (2.22 g.; 2.0 mmole) was carried through the procedures in Tables I and II using 2 deblockings (5 minutes and 25 minutes) with 50% TFA in methylene chloride and 2.5 equivalents of BOC-amino acid in the required sequence until the desired BOC-tetrapeptide-O-CH$_2$-φ-resin was obtained.

DCCI (dicyclohexylcarbodi-imide) was used as the sole coupling agent in every step. The coupling of each amino acid proceeded smoothly.

The coupling reactions were carried out in methylene chloride, freshly degassed DMF or a mixture of those two solvents. Two equivalents 1-hydroxybenzotriazole/equivalent of BOC-amino acid were added where DMF was the solvent.

The resin peptide prepared as described above was then treated by ammonolysis as described in the remaining portion of this step.

TABLE I

| Solvent or reagent (number of treatments or washes) | CH$_2$Cl$_2$ (3) | 50% TFA CH$_2$Cl$_2$* + 5% EDT (2) | CH$_2$Cl$_2$ (3) | CHCl$_3$ (3) | NET$_3$— CHCl$_3$ (1:9) (1) | CHCl$_3$(3) CH$_2$Cl$_2$(3) | BOC AA in CH$_2$Cl$_2$, DMF or a mixture of both | 0.5M DCCI in CH$_2$Cl$_2$ | MeOH CHCl$_3$ (3 each alternating |
|---|---|---|---|---|---|---|---|---|---|
| Volume in ml. | 45 | 45 | 45 | 45 | 45 | 45 | 25 | 10 | 45 |
| Time in min. | 2 | 5 and 25 | 2 | 2 | 10 | 2 | 5 | 5 coupling 2 hours | 5 |

*EDT = Ethanedithiol

TABLE II

| Protected Amino Acid | Solvent Ml. |
|---|---|
| BOC-Phe 1.32 g.) | 25 ml. CH$_2$Cl$_2$ |
| 2-[R-(3-BOC-amino-2-oxo-1-azepine) acetic acid] (1.45 g.) | 25 ml. DMF |

The resin peptide was suspended in 25 ml. of methanol and the reaction mixture was saturated with ammonia at 0° C. The pressure bottle was capped and stirred at room temperature for 3 days, during which time a solid crystallized. The mixture was filtered and the crystalline material and resin peptide were washed with methanol. The crystals were then washed away from the resin with dimethylformamide. Concentration of the dimethylformamide solution in vacuo and recrystallization of the residue from dichloromethane/ethyl acetate/hexane gave a first crop of 589 mg. having a m.p. of 208° (dec.), and a second crop of 741 mg. for a total yield of 66%.

Concentration of the methanol mother liquor from the reaction and combination with the small amount of residue from the mother liquor for the second crop of crystals gave a residue from which further crystallization of product by seeding was attempted. Two additional crops of 51 mg. and 118 mg. were obtained.

D. Deblocking to give 2-[R-(3-amino-2-oxo-1-azepine) acetic acid]-Phe-Met-NH$_2$ hydrochloride A 673 mg. (1.20 mmole) sample of the product obtained in Step C. above was slurried in 30 ml. of ethyl acetate, then cooled to 0° C. under nitrogen. Hydrogen chloride gas was bubbled through the reaction mixture for 15 min. during which time the sample dissolved and reprecipitated. Nitrogen was then bubbled through for 1 hr., after which the reaction mixture was filtered, and the solid residue was washed with small portions of ethyl acetate. The solid was dried in vacuo to give 578 mg. (97% yield) of product.

E. BOC-Tyr-2-[R-(3-amino-2-oxo-1-azepine)acetic acid]-Phe-Met-NH$_2$

A 559 mg. (1.12 mmole) sample of the product obtained in Step D. above and 444 mg. (1.18 mmole) of BOC-Tyr-hydroxysuccinimide ester (HSE) were dissolved in 10 ml. of degassed dimethylformamide under nitrogen. Triethylamine (100 μl) was added to achieve a pH of about 8.5. After 2 hrs. the reaction was about 50% complete and after 23 hrs., little further change had occurred. The pH had dropped to about 7, so an additional 25 μl. of triethylamine was added along with more BOC-Tyr-HSE (149 mg., 0.4 mmole). Some precipitate formed when the triethylamine was added. The reaction mixture was stirred an additional hour during which time an additional 40 ml. of triethylamine was added. At this point the reaction was essentially complete, and the reaction mixture was poured into 100 ml. of water. The resulting mixture was extracted three times with 50 ml. of dichloromethane. These extracts were combined and dried over sodium sulfate, filtered, and concentrated in vacuo to a colorless, very viscous oil. This material was dissolved in dichloromethane/ethyl acetate and taken to a cloud point with 1:1 ethyl acetate/hexane. After standing overnight in the freezer, a gum had separated, and this gum was washed twice with small portions of ethyl acetate. Dissolution of the gum in dichloromethane and concentration in vacuo gave 450 mg. of a foam, a yield of 55%.

F. H-Tyr-2-[R-(2-oxo-1-azepine)acetic acid]-Phe-Met-NH$_2$

A 408 mg. (0.56 mmole) sample of the product obtained in Step E. above was treated for 15 min. at room temperature with 16 ml. of 3:1 trifluoroacetic acid/ethanedithiol. The solution was concentrated in vacuo to a semisolid residue weighing 700 mg. which was dissolved in warm isopropanol, and the resulting solution was allowed to stand overnight at 0° C. A white semisolid separated which melted on filtration. This material was recombined with the mother liquor and the whole sample was chromatographed on 75 g. of silica gel, eluting with 15:5.1:2 ethyl acetate/pyridine/acetic acid/water. Chromatographic fractions 16–24 were combined and precipitated from ethanol/ether to give 241 mg. (58% yield) of product.

EXAMPLE 4

H-Tyr-2-[R-(3-amino-2-oxo-1-pyrrolidine)acetic acid]-Phe-Met-NH$_2$

A. Methylation of BOC-R-Met-Gly-OMe to form sulfonium salt

A 9.73 g. sample of BOC-R-Met-Gly-OMe was dissolved with stirring in 60 ml. of methyl iodide for 7 hrs. The reaction mixture was concentrated in vacuo and washed three times with water and refoamed from dichloromethane to give 11.96 g. of product, a 92% yield.

B. 2-[R-(3-BOC-amino-2-oxo-1-pyrrolidine)acetic acid]

The sulfonium salt product obtained in Step A. above was placed in a 3-neck liter flask and dissolved in 500 ml. of 1:1 dimethylformamide/dichloromethane under nitrogen. The reaction mixture was cooled to 0° C. and 2.5 g. of a 50% dispersion of sodium hydride in mineral oil was added in one portion. After 2 hrs., 166 ml. of methyl acetate and about 3 ml. of water were added, and the reaction mixture was allowed to stand overnight. Some salt precipitated which was dissolved in water, acidified, and extracted with dichloromethane. The remaining mother liquor was partitioned with dichloromethane/water. The dichloromethane partition was concentrated and subjected to thin layer chromatography using 1:1 ethyl acetate/hexane. The acidified aqueous phase was placed in a continuous extractor and extracted with dichloromethane for 24 hrs. The dichloromethane extracts were concentrated to crystallization on a roto-evaporator, and the product was recrystallized from dichloromethane/ethyl acetate to give 723.5 mg. of product.

C. 2-[R-(3-BOC-amino-2-oxo-1-pyrrolidine)acetic acid]-Phe-Met-NH$_2$

BOC-Phe-Met-OR was prepared in accordance with the procedures described in Example 3, Step C. above; and 12.2 g. of this material was added to 2.06 g. of the product obtained in Step B. immediately above in accordance with the sequence of solid phase synthesis procedures and reagents set out in the following chart; followed by the ammonolysis procedure described in Example 3, Step C. above.

TABLE III

| Reagent | CH$_2$Cl$_2$ Wash 3× | 50% TFA in CH$_2$Cl$_2$ 2× | CH$_2$Cl$_2$ 3× | CHCl$_3$ 3× | Et$_3$N: CHCl$_3$ 1:9 | CHCl$_3$ Wash 3× | CH$_2$Cl$_2$ Wash 3× | Lactam* in CH$_2$Cl$_2$ | DCCI** 1 g./2 ml. CH$_2$Cl$_2$ | CH$_3$OH and CH$_2$Cl$_2$ washes 3× each |
|---|---|---|---|---|---|---|---|---|---|---|
| Volume (ml.) | 100 | 100 | 100 | 100 | 100 | 100 | 100 | 50 | 9.27 | 100 |
| Time (min.) | 2 | 5 25 | 2 | 2 | 10 | 2 | 2 | 5 | 2 hrs. | 2 |

*2-[R-(3-BOC-amino-2-oxo-1-pyrrolidine)acetic acid]
**DCCI = Dicyclohexylcarbodi-imide

D. Deblocking of 2-[R-(3-BOC-amino-2-oxo-1-pyrrolidine) acetic acid]-Phe-Met-NH$_2$ A 982 mg. sample of the product obtained in Step C. above was placed in 50 ml. of ethyl acetate and nitrogen was bubbled through for about 30 min. while cooling to 0° C. with stirring. Hydrogen chloride gas was bubbled through the reaction mixture for more than 20 min. and a white precipitate resulted. Nitrogen was bubbled through for 2 hrs. to remove excess hydrogen chloride gas. The precipitate was filtered to yield 878 mg. of product as hydrochloride salt, a 93% yield.

E. BOC-Tyr-2-[R-(3-amino-2-oxo-1-pyrrolidine)acetic acid]-Phe-Met-NH$_2$

A 544 mg. (1.20 mmole) sample of the hydrochloride salt product obtained in Step D. above, 476 mg. (1.26 mmole) of hydroxysuccinimide ester of BOC-protected Tyr (BOC-Tyr-HSE), and 10 ml. of degassed dimethylformamide were stirred under nitrogen and the pH of the reaction mixture was brought up to 8.5 with triethylamine, where it was maintained for 16 hrs. by further additions of triethylamine. The solids were filtered, added to 100 ml. of water, and extracted three times with dichloromethane, and the extracts were concentrated in vacuo. The product was crystallized out during concentration, then recrystallized from methanol/ethyl acetate/hexane to give 562 mg., an 81% yield.

F. H-Tyr-2-[R-(3-amino-2-oxo-1-pyrrolidine)acetic acid]-Phe-Met-NH$_2$ hydrochloride A 500 mg. sample of the product obtained in Step E. above was slurried in 30 ml. of ethyl acetate and nitrogen was bubbled through the reaction mixture while cooling to 0° C. Hydrogen chloride gas then bubbled through the reaction mixture with stirring for 25 min., followed by nitrogen for 2 hrs. at room temperature. The solid was filtered and dried in vacuo to give 370.6 mg. of product, an 82% yield.

What is claimed is:

1. A novel peptide of the formula:

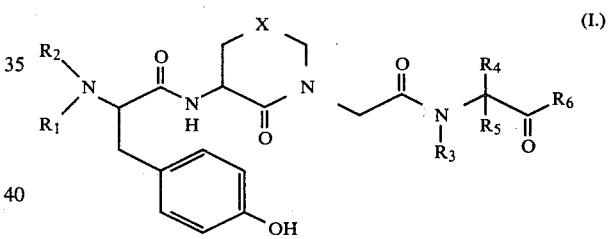

(I.)

where, unless otherwise indicated, an amino acid substituent identified below has the "S—" stereoconfiguration:

X is S or (CH$_2$)$_n$, where n is 0, 1 or 2;

R$_1$ is hydrogen; C$_{1-6}$ alkyl; H-Arg; or H-Lys-Arg;

R$_2$ is hydrogen; C$_{1-6}$ alkyl; or, when R$_1$ is hydrogen, may be allyl or cyclopropylmethyl;

R$_3$ is hydrogen or methyl;

R$_4$ is benzyl; benzyl substituted with halo, nitro, hydroxy, amino, C$_{1-4}$ alkyl, or cyano; indolylmethyl; imidazolylmethyl; or isopropylmethyl;

R$_5$ is hydrogen or methyl;

R$_4$ and R$_5$ taken together are phenylmethylene; and $R_6$ is (a) OM, where M is hydrogen, $C_{1-6}$ alkyl, or a cation; (b) $NR_7R_8$, where $R_7$ and $R_8$ are independently selected from the group consisting of hydrogen; $C_{1-6}$ alkyl, and, when either of $R_7$ or $R_8$ is hydrogen, $-CH_2CH_2N(CH_3)_2$ and

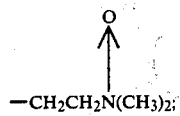

(c) Met-OH; (d) Met-$NH_2$; (e) Met-ol; (f) D-Met-$NH_2$; (g) N-methyl-Met-$NH_2$; (h) Met(O)-$NH_2$; (i) Met(O)-ol; (j) Leu-$NH_2$; (k) N-methyl-Leu-$NH_2$; (l) D-Leu-$NH_2$; or (m) Pro-$NH_2$.

2. A peptide according to claim 1 wherein:
X is S or $(CH_2)_n$ where n is 1 and the resulting lactam has an "R" stereoconfiguration; and
$R_1$ and $R_2$ are hydrogen;
$R_3$ and $R_5$ are hydrogen or methyl;
$R_4$ is benzyl;
$R_4$ and $R_5$ taken together are phenylmethylene; and
$R_6$ is $NR_7R_8$ where one of $R_7$ or $R_8$ is hydrogen and the other is $-CH_2CH_2N(CH_3)_2$ or

Met-OH; Met-$NH_2$; Met-ol; D-Met-$NH_2$; N-methyl-Met-$NH_2$; Met(O)-$NH_2$; Met(O)-ol; Leu-$NH_2$; N-methyl-Leu-$NH_2$; D-Leu-$NH_2$; or Pro-$NH_2$.

3. A peptide according to claim 1 wherein the peptide is H-Tyr-2-[R-(3-amino-2-oxo-1-piperidine)acetic acid]-[N-methyl-Phe]-Met-$NH_2$.

4. A peptide according to claim 1 wherein the peptide is H-Tyr-2-[R-(3-amino-2-oxo-1-piperidine)acetic acid]-[Nmethyl-Phe]-Met-ol.

5. A peptide according to claim 1 wherein the peptide is H-Tyr-2-[R-(3-amino-2-oxo-1-piperidine)acetic acid]-[N-methyl-Phe]-Met(O)-$NH_2$.

6. A peptide according to claim 1 wherein the peptide is H-Tyr-2-[R-(3-amino-2-oxo-1-piperidine)acetic acid]-[N-methyl-Phe]-Met(O)-ol.

7. A peptide according to claim 1 wherein the peptide is H-Tyr-2-[R-(3-amino-2-oxo-1-piperidine)acetic acid]-[N-methyl-Phe]-N-methyl-Met-$NH_2$.

8. A peptide according to claim 1 wherein the peptide is H-Tyr-2-[R-(3-amino-2-oxo-1-piperidine)acetic acid]-[N-methyl-Phe]-D-Met-$NH_2$.

9. A peptide according to claim 1 wherein the peptide is H-Tyr-2-[R-(3-amino-2-oxo-1-piperidine)acetic acid]-[N-methyl-Phe]-Leu-$NH_2$.

10. A peptide according to claim 1 wherein the peptide is H-Tyr-2-[R-(3-amino-2-oxo-1-piperidine)acetic acid]-[Nmethyl-Phe]-N-methyl-Leu-$NH_2$.

11. A peptide according to claim 1 wherein the peptide is H-Tyr-2-[R-(3-amino-2-oxo-1-piperidine)acetic acid]-[N-methyl-Phe]-D-Leu-$NH_2$.

12. A peptide according to claim 1 wherein the peptide is H-Tyr-2-[R-(3-amino-2-oxo-1-piperidine)acetic acid]-[N-methyl-Phe]-Pro-$NH_2$.

13. A peptide according to claim 1 wherein the peptide is H-Tyr-2-[R-(3-amino-2-oxo-1-piperidine)acetic acid]-[N-methyl-Phe]

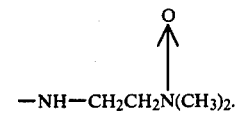

14. A peptide according to claim 1 wherein the peptide is H-Tyr-2-[R-(3-amino-2-oxo-1-piperidine)acetic acid]-[N-methyl-Phe]-NH-$CH_2CH_2N(CH_3)_2$.

15. A peptide according to claim 1 wherein the peptide is H-Tyr-2-[R-(3-amino-2-oxo-1-piperidine)acetic acid]-[α-methyl-Phe]-Met-$NH_2$.

16. A peptide according to claim 1 wherein the peptide is H-Tyr-2-[R-(3-amino-2-oxo-1-piperidine)acetic acid]-[α-methyl-Phe]-Met-ol.

17. A peptide according to claim 1 wherein the peptide is H-Tyr-2-[R-(3-amino-2-oxo-1-piperidine)acetic acid]-[α-methyl-Phe]-Met(O)-$NH_2$.

18. A peptide according to claim 1 wherein the peptide is H-Tyr-2-[R-(3-amino-2-oxo-1-piperidine)acetic acid]-[α-methyl-Phe]-Met(O)-ol.

19. A peptide according to claim 1 wherein the peptide is H-Tyr-2-[R-(3-amino-2-oxo-1-piperidine)acetic acid]-[α-methyl-Phe]-N-methyl-Met-$NH_2$.

20. A peptide according to claim 1 wherein the peptide is H-Tyr-2-[R-(3-amino-2-oxo-1-piperidine)acetic acid]-[α-methyl-Phe]-D-Met-$NH_2$.

21. A peptide according to claim 1 wherein the peptide is H-Tyr-2-[R-(3-amino-2-oxo-1-piperidine)acetic acid]-[α-methyl-Phe]-Leu-$NH_2$.

22. A peptide according to claim 1 wherein the peptide is H-Tyr-2-[R-(3-amino-2-oxo-1-piperidine)acetic acid]-[α-methyl-Phe]-N-methyl-Leu-$NH_2$.

23. A peptide according to claim 1 wherein the peptide is H-Tyr-2-[R-(3-amino-2-oxo-1-piperidine)acetic acid]-[α-methyl-Phe]-D-Leu-$NH_2$.

24. A peptide according to claim 1 wherein the peptide is H-Tyr-2-[R-(3-amino-2-oxo-1-piperidine)acetic acid]-[α-methyl-Phe]-Pro-$NH_2$.

25. A peptide according to claim 1 wherein the peptide is H-Tyr-2-[R-(3-amino-2-oxo-1-piperidine)acetic acid]-[α-methyl-Phe]

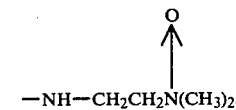

26. A peptide according to claim 1 wherein the peptide is H-Tyr-2-[R-(3-amino-2-oxo-1-piperidine)acetic acid]-[α-methyl-Phe]-NH-$CH_2CH_2N(CH_3)_2$.

27. A peptide according to claim 1 wherein the peptide is H-Tyr-2-[R-(3-amino-2-oxo-1-piperidine)acetic acid]-[2,3-dehydro Phe]-Met-$NH_2$.

28. A peptide according to claim 1 wherein the peptide is H-Tyr-2-[R-(3-amino-2-oxo-1-piperidine)acetic acid]-[2,3-dehydro Phe]-Met(O)-ol.

29. A peptide according to claim 1 wherein the peptide is H-Tyr-2-[R-(3-amino-2-oxo-1-piperidine)acetic acid]-2,3-dehydro Phe]-N-methyl-Leu-$NH_2$.

30. A peptide according to claim 1 wherein the peptide is H-Tyr-2-[R-(3-amino-2-oxo-1-piperidine)acetic acid]-[2,3-dehydro Phe]

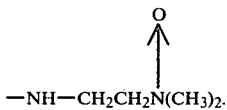

31. A peptide according to claim 1 wherein the peptide is H-Tyr-2-[R-(3-amino-2-oxo-1-piperidine)acetic acid]-[2,3-dehydro Phe]-NH-CH$_2$CH$_2$N(CH$_3$)$_2$.

32. A peptide according to claim 1 wherein the peptide is H-Tyr-2-[R(5-amino-4-oxo-1,3-thiazine)acetic acid]-[N-methyl-Phe]-Met-NH$_2$.

33. A peptide according to claim 1 wherein the peptide is H-Tyr-2-[R-(5-amino-4-oxo-1,3-thiazine)acetic acid]-[N-methyl-Phe]-Met(O)-ol.

34. A peptide according to claim 1 wherein the peptide is H-Tyr-2-[R(5-amino-4-oxo-1,3-thiazine)acetic acid]-[N-methyl-Phe]-N-methyl-Leu-NH$_2$.

35. A peptide according to claim 1 wherein the peptide is H-Tyr-2-[R-(5-amino-4-oxo-1,3-thiazine)acetic acid]-N-methyl-Phe]

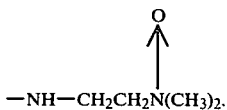

36. A peptide according to claim 1 wherein the peptide is H-Tyr-2[R-(5-amino-4-oxo-1,3-thiazine)acetic acid]-[N-methyl-Phe]-NH-CH$_2$CH$_2$N(CH$_3$)$_2$.

37. A pharmaceutical composition for treating pain comprising a non-toxic, pharmaceutically acceptable carrier and a therapeutically effective amount of a peptide of the formula:

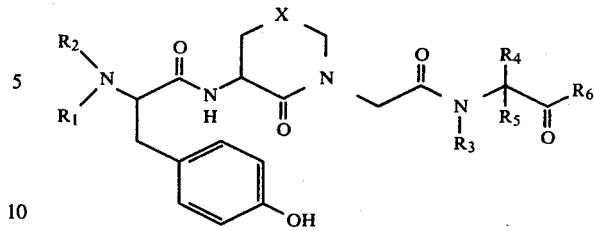

where, unless otherwise indicated, an amino acid substitutent identified below has the "S—" stereoconfiguration:

X is S or (CH$_2$)$_n$, where n is 0, 1 or 2;

R$_1$ is hydrogen; C$_{1-6}$ alkyl; H-Arg; or H-Lys-Arg;

R$_2$ is hydrogen; C$_{1-6}$ alkyl; or, when R$_1$ is hydrogen, may be allyl or cyclopropylmethyl;

R$_3$ is hydrogen or methyl;

R$_4$ is benzyl; benzyl substituted with halo, nitro, hydroxy, amino, C$_{1-4}$ alkyl, or cyano; indolylmethyl; imidazolylmethyl; or isopropylmethyl;

R$_5$ is hydrogen or methyl;

R$_4$ and R$_5$ taken together are phenylmethylene; and

R$_6$ is (a) OM, where M is hydrogen, C$_{1-6}$ alkyl, or a cation; (b) NR$_7$R$_8$, where R$_7$ and R$_8$ are independently selected from the group consisting of hydrogen; C$_{1-6}$ alkyl, and, when either of R$_7$ or R$_8$ is hydrogen, —CH$_2$CH$_2$N(CH$_3$)$_2$ and

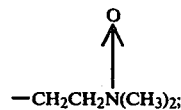

(c) Met-OH; (d) Met-NH$_2$; (e) Met-ol; (f) D-Met-NH$_2$; (g) N-methyl-Met-NH$_2$; (h) Met(O)—NH$_2$; (i) Met(O)-ol; (j) Leu-NH$_2$; (k) N-methyl-Leu-NH$_2$; (l) D-Leu-NH$_2$; or (m) Pro-NH$_2$.

* * * * *